United States Patent
Hopkins et al.

(10) Patent No.: US 8,246,580 B2
(45) Date of Patent: Aug. 21, 2012

(54) ASPIRATION CONTROL VIA FLOW OR IMPEDANCE

(75) Inventors: Mark A. Hopkins, Mission Viejo, CA (US); John C. Huculak, Mission Viejo, CA (US); Kirk W. Todd, Yorba Linda, CA (US); Roger Thomas, Tustin, CA (US); Shawn X. Gao, Irvine, CA (US); Nader Nazarifar, Laguna Niguel, CA (US)

(73) Assignee: Novartis AG, Basel (CH)

( * ) Notice: Subject to any disclaimer, the term of this patent is extended or adjusted under 35 U.S.C. 154(b) by 170 days.

(21) Appl. No.: 12/545,392

(22) Filed: Aug. 21, 2009

(65) Prior Publication Data

US 2010/0030168 A1  Feb. 4, 2010

Related U.S. Application Data

(62) Division of application No. 11/158,259, filed on Jun. 21, 2005, now abandoned.

(51) Int. Cl.
*A61M 1/00* (2006.01)
*A61M 31/00* (2006.01)

(52) U.S. Cl. ............... 604/118; 604/65; 604/30; 604/35

(58) Field of Classification Search .................... 604/30, 604/35, 65–67, 503, 505; 606/107, 166, 606/170
See application file for complete search history.

(56) References Cited

U.S. PATENT DOCUMENTS

| | | |
|---|---|---|
| 3,670,754 A | 6/1972 | Freeman |
| 4,041,947 A | 8/1977 | Weiss et al. |
| 4,210,029 A | 7/1980 | Porter |
| 4,548,205 A | 10/1985 | Armeniades et al. |
| 4,722,350 A | 2/1988 | Armeniades et al. |
| 4,770,187 A | 9/1988 | Lash et al. |
| 4,823,552 A | 4/1989 | Ezell et al. |
| 4,841,984 A | 6/1989 | Armeniades et al. |
| 4,935,005 A | 6/1990 | Haines |
| 5,098,387 A | 3/1992 | Wiest et al. |
| 5,141,493 A | 8/1992 | Jacobsen et al. |
| 5,242,404 A | 9/1993 | Conley et al. |
| 5,322,504 A | 6/1994 | Doherty et al. |
| 5,380,280 A | 1/1995 | Peterson |
| 5,399,166 A | 3/1995 | Laing |
| 5,403,276 A | 4/1995 | Schechter et al. |
| 5,656,027 A | 8/1997 | Ellingboe |
| 5,674,194 A | 10/1997 | Jung et al. |
| 5,676,650 A | 10/1997 | Grieshaber et al. |
| 5,697,898 A | 12/1997 | Devine |
| 5,733,256 A | 3/1998 | Costin |
| 5,747,824 A | 5/1998 | Jung et al. |
| 5,865,764 A | 2/1999 | Moorhead |
| 6,251,113 B1 | 6/2001 | Appelbaum et al. |
| 6,413,022 B1 | 7/2002 | Sarh |
| 6,743,636 B2 * | 6/2004 | Chung et al. .................. 436/100 |
| 2002/0019607 A1 | 2/2002 | Bui |
| 2006/0224143 A1 | 10/2006 | Claus et al. |

FOREIGN PATENT DOCUMENTS

| | | |
|---|---|---|
| WO | 93/17729 A1 | 9/1993 |
| WO | 93/18802 A1 | 9/1993 |

\* cited by examiner

*Primary Examiner* — Christopher D Koharski
*Assistant Examiner* — Rebecca E Eisenberg
(74) *Attorney, Agent, or Firm* — W. David Lee

(57) ABSTRACT

A microsurgical system capable of controlling aspiration and detecting an occlusion via monitoring a change in either suction flow rate or suction impedance.

9 Claims, 1 Drawing Sheet

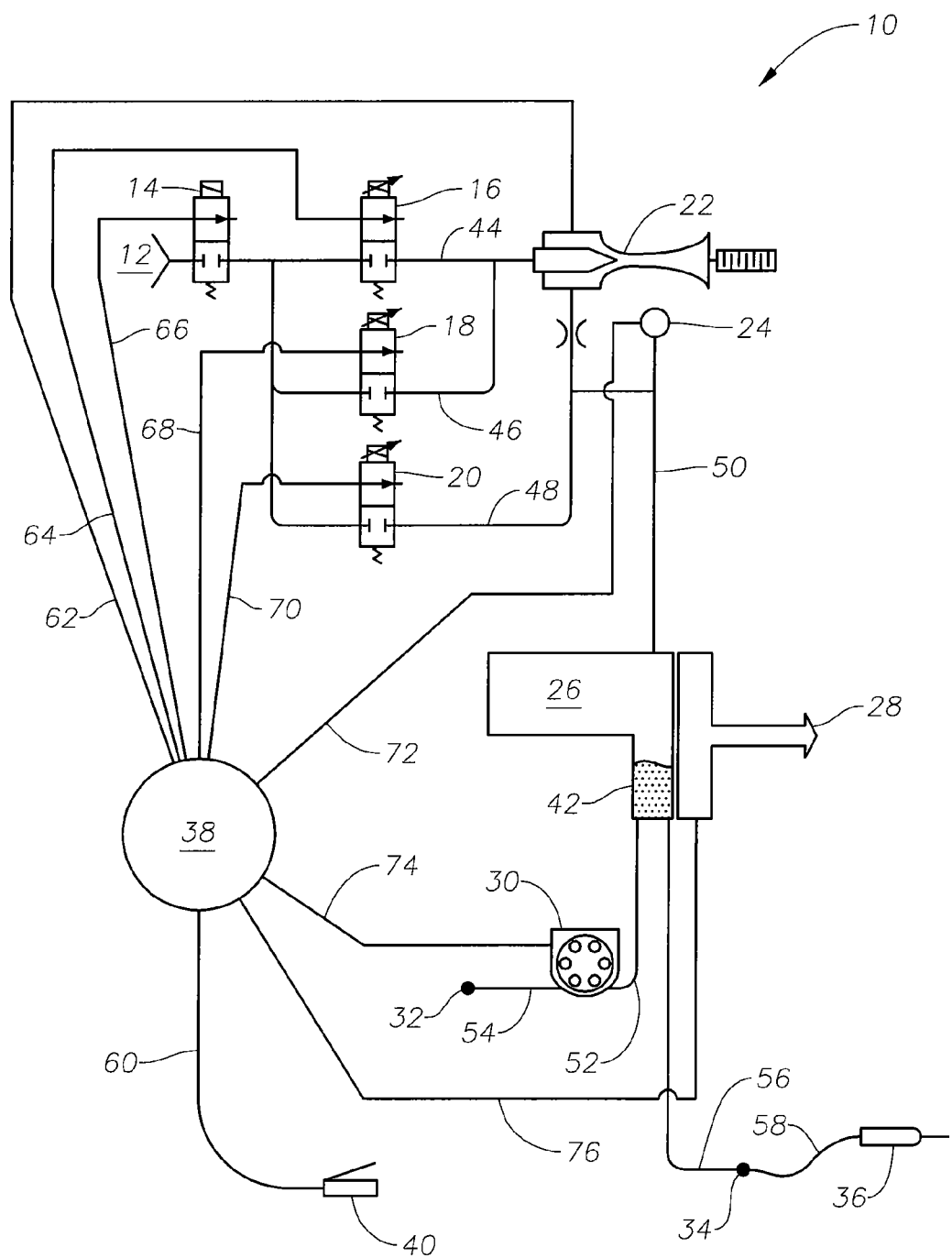

ASPIRATION CONTROL VIA FLOW OR IMPEDANCE

This application is a divisional application of U.S. application Ser. No. 11/158,259 filed Jun. 21, 2005 now abandoned.

FIELD OF THE INVENTION

The present invention generally pertains to controlling aspiration in microsurgical systems and more particularly to controlling aspiration in ophthalmic microsurgical systems.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site. Varying surgical conditions and surgical objectives can lead to varying amounts of effort required to effectively and safely remove the tissue and fluid.

The types of aspiration systems used, prior to the present invention, were generally characterized as either flow controlled or vacuum controlled, depending upon the type of pump used in the system. Each type of system has certain advantages.

Vacuum controlled aspiration systems are operated by setting a desired vacuum level, which the system seeks to maintain. Flow rate is dependent on intraocular pressure, vacuum level, and resistance to flow in the fluid path. Actual flow rate information is unavailable. Vacuum controlled aspiration systems typically use a venturi or diaphragm pump. Vacuum controlled aspiration systems offer the advantages of quick response times, control of decreasing vacuum levels, and good fluidic performance while aspirating air, such as during an air/fluid exchange procedure. Disadvantages of such systems are the lack of flow information resulting in transient high flows during phacoemulsification or fragmentation coupled with a lack of occlusion detection. Vacuum controlled systems are difficult to operate in a flow controlled mode because of the problems of non-invasively measuring flow in real time.

Flow controlled aspiration systems are operated by setting a desired aspiration flow rate for the system to maintain. Flow controlled aspiration systems typically use a peristaltic, scroll, or vane pump. Flow controlled aspiration systems offer the advantages of stable flow rates and automatically increasing vacuum levels under occlusion. Disadvantages of such systems are relatively slow response times, undesired occlusion break responses when large compliant components are used, and vacuum can not be linearly decreased during tip occlusion. Flow controlled systems are difficult to operate in a vacuum controlled mode because time delays in measuring vacuum can cause instability in the control loop, reducing dynamic performance.

One currently available ophthalmic surgical system, the MILLENIUM system from Storz Instrument Company, contains both a vacuum controlled aspiration system (using a venturi pump) and a separate flow controlled aspiration system (using a scroll pump). The two pumps can not be used simultaneously, and each pump requires separate aspiration tubing and cassette.

Another currently available ophthalmic surgical system, the ACCURUS® system from Alcon Laboratories, Inc., contains both a venturi pump and a peristaltic pump that operate in series. The venturi pump aspirates material from the surgical site to a small collection chamber. The peristaltic pump pumps the aspirate from the small collection chamber to a larger collection bag. The peristaltic pump does not provide aspiration vacuum to the surgical site. Thus, the system operates as a vacuum controlled system.

Accordingly, a need continues to exist for an improved method of effectively and safely removing aspirated tissue and fluid in a microsurgical system.

SUMMARY OF THE INVENTION

The present invention is a method of controlling aspiration in a microsurgical system. A desired suction flow rate is created in an aspiration chamber using a pressurized gas source, a vacuum generator, and a pump. Fluid is aspirated from a surgical device into the aspiration chamber. An actual level of the fluid is determined in the aspiration chamber.

In one aspect of the present invention, a suction flow rate is calculated in response to the actual level of fluid. A change in the suction flow rate is monitored to detect an occlusion.

In another aspect of the present invention, a suction impedance is calculated in response to the suction flow rate. A change in the suction impedance is monitored to detect an occlusion.

BRIEF DESCRIPTION OF THE DRAWINGS

For a more complete understanding of the present invention, and for further objects and advantages thereof, reference is made to the following description taken in conjunction with the accompanying drawing, in which FIG. 1 is a schematic diagram illustrating aspiration control in a microsurgical system.

DETAILED DESCRIPTION OF THE PREFERRED EMBODIMENTS

The preferred embodiment of the present invention and its advantages is best understood by referring to FIG. 1 of the drawings. Microsurgical system 10 includes a pressurized gas source 12, an isolation valve 14, a vacuum proportional valve 16, an optional second vacuum proportional valve 18, a pressure proportional valve 20, a vacuum generator 22, a pressure transducer 24, an aspiration chamber 26, a fluid level sensor 28, a pump 30, a collection bag 32, an aspiration port 34, a surgical device 36, a computer or microprocessor 38, and a proportional control device 40. The various components of system 10 are fluidly coupled via fluid lines 44, 46, 48, 50, 52, 54, 56, and 58. The various components of system 10 are electrically coupled via interfaces 60, 62, 64, 66, 68, 70, 72, 74, and 76. Valve 14 is preferably an "on/off" solenoid valve. Valves 16-20 are preferably proportional solenoid valves. Vacuum generator 22 may be any suitable device for generating vacuum but is preferably a vacuum chip or a venturi chip that generates vacuum when isolation valve 14 and vacuum proportional valves 16 and/or 18 are open and gas from pressurized gas source 12 is passed through vacuum generator 22. Pressure transducer 24 may be any suitable device for directly or indirectly measuring pressure and vacuum. Fluid level sensor 28 may be any suitable device for measuring the level of a fluid 42 within aspiration chamber 26 but is preferably capable of measuring fluid levels in a continuous manner. Pump 30 may be any suitable device for generating vacuum but is preferably a peristaltic pump, a scroll pump, or a vane pump. Microprocessor 38 is capable of implementing feedback control, and preferably PID control. Proportional controller 40 may be any suitable device for proportionally controlling system 10 and/or surgical device 36 but is preferably a foot controller.

System 10 preferably utilizes three distinct methods of controlling aspiration, vacuum control, suction control, and flow control. In vacuum control mode, microprocessor 38 activates isolation valve 14 via interface 66 and maintains pressure valve 20 in a closed state via interface 70. Proportional controller 40 and microprocessor 38 are used to proportionally open or close vacuum proportional valve 16 (and optionally vacuum proportional valve 18, for higher levels of vacuum) via interfaces 60, 64, and 68. A surgeon inputs a maximum vacuum level into microprocessor 38. Using proportional controller 40, the surgeon may then proportionally vary the desired vacuum provided to surgical device 36 and aspiration chamber 26 via vacuum generator 22 between zero and the maximum value. As aspiration chamber 26 fills with fluid 42 aspirated by surgical device 36, pressure transducer 24 measures the actual vacuum in aspiration chamber 26 and provides a corresponding signal to microprocessor 38 via interface 72. Microprocessor 38 in turn provides feedback signals to valves 16 and 18 via interfaces 64 and 68 to maintain the vacuum at the desired level indicated by proportional controller 40.

In the suction control mode, microprocessor 38 activates valves 14, 16, 18, and 20. System 10 is configured to provide a range of suction to surgical device 36 and aspiration chamber 26 from a small positive value of pressure to a larger negative value of pressure (or vacuum). This range is preferably from about +150 mm Hg to about −650 mm Hg. Using proportional controller 40, a surgeon may proportionally vary the desired suction provided to surgical device 36 and aspiration chamber 26 via pressurized gas source 12 and vacuum generator 22 in this range. A signal corresponding to the desired suction is provided to microprocessor 38 via interface 60. Pressure transducer 24 provides a signal corresponding to the actual suction pressure in aspiration chamber 26 to microprocessor 38 via interface 72. Microprocessor 38 then provides feedback signals to any combination of valves 16, 18, and 20 via interfaces 64, 68, and 70, respectively, to maintain the suction within aspiration chamber 26 and surgical device 36 at the desired level. As one skilled in the art will appreciate, the suction control mode allows microprocessor 38 to close valves 16 and 18 and open valve 20 to create a pressure within aspiration chamber 26 equal to the intraocular pressure so as to prevent passive flow from the eye into surgical device 36 and aspiration chamber 26.

In the flow control mode, microprocessor 38 activates valves 14, 16, 18, and 20. System 10 is configured to provide a range of flow to surgical device 36 and aspiration chamber 26 from a value of zero flow to a maximum value of flow. Using proportional controller 40, a surgeon may proportionally vary the desired suction flow rate for surgical device 36 and aspiration chamber 26 in this range. Flow rate is calculated using the following equation:

$$Q_{suction} = Q_{pump}(N,P) + A\, dz/dt,$$

where $Q_{suction}$ is the suction flow rate, $Q_{pump}$ is the flow rate of pump 30, N is the speed of pump 30, P is the suction pressure measured by pressure transducer 24, A is the cross-sectional area of aspiration chamber 26, and Z is the level of fluid 42 in aspiration chamber 26 measured via fluid level sensor 28. A signal corresponding to the desired $Q_{suction}$ is provided to microprocessor 38 via interface 60. Microprocessor 38 provides a signal corresponding to pump speed N to pump 30 via interface 74 in response to the desired $Q_{suction}$. Fluid level sensor 28 provides a signal corresponding to the actual level of fluid within aspiration chamber 26 to microprocessor 38 via interface 76. Microprocessor 38 uses the suction control mode, as described above, to maintain $Q_{suction}$ at the desired level. More specifically, microprocessor 38 calculates $Q_{suction}$ in response to the actual level of fluid within aspiration chamber 26 and provides feedback signals to any combination of valves 16, 18, and 20 via interfaces 64, 68, and 70, respectively, so as to maintain $Q_{suction}$ at the desired level. As part of the suction control mode, pressure transducer 24 provides a signal corresponding to the actual suction pressure P in aspiration chamber 26 to microprocessor 38 via interface 72. As one skilled in the art will appreciate, the flow control mode allows microprocessor 38 to maintain a constant level of fluid 42 in aspiration chamber 26 (dz/dt=0) so as to maintain flow rate.

In the suction control mode, suction impedance can be defined as follows:

$$I = (P_{suction} - P_{reference})/Q_{suction},$$

where I is the suction impedance, $Q_{suction}$ is the suction flow rate, $P_{suction}$ is the suction pressure P measured by pressure transducer 24, and $P_{reference}$ is a reference pressure, such as intraocular pressure in an aspiration circuit of a microsurgical system, or infusion pressure, irrigation pressure, or atmospheric pressure in the infusion circuit of a microsurgical system. As discussed hereinabove, traditional vacuum controlled aspiration systems are not capable of occlusion detection in the aspiration circuit, and traditional flow based aspiration systems detect occlusion in the aspiration circuit by monitoring change in measured vacuum. It has been discovered that monitoring change in $Q_{suction}$ or I is a more effective and safe way of detecting occlusion in an aspiration circuit of a microsurgical system. Detecting occlusion by monitoring change in $Q_{suction}$ or I gives a surgeon a better idea of the characteristics of the material that is causing the occlusion. Monitoring change in I is believed to be preferred over monitoring change in $Q_{suction}$. Preferably, microprocessor 38 monitors such change in $Q_{suction}$ or I in real time.

Once an occlusion is detected by monitoring change in $Q_{suction}$ or I, microprocessor 38 may automatically adjust other surgical parameters in order to improve the speed and safety of the surgical procedure. For example, if surgical device 36 is a phacoemulsification probe, ultrasound energy, desired suction pressure, desired suction flow rate, and/or infusion pressure may be adjusted real-time as either $Q_{suction}$ or I changes. As another example, if surgical device 36 is a vitrectomy probe, cut rate, port open duty cycle, desired suction pressure, desired suction flow rate, and/or infusion pressure may be adjusted real time as either $Q_{suction}$ or I changes. In addition, microprocessor 38 may use changes in I to communicate fluid or tissue properties such as viscosity to the surgeon via an appropriate sense (e.g. audibly, visually, or tactilely).

The present invention is illustrated herein by example, and various modifications may be made by a person of ordinary skill in the art. For example, while the present invention is described above relative to detecting occlusion in the aspiration circuit of a microsurgical system, it is also applicable to detecting occlusion in the infusion circuit of a microsurgical system.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of controlling aspiration in a microsurgical system, comprising the steps of:
providing a pump speed to a peristaltic pump with a computer;
determining an actual level of fluid in an aspiration chamber with a fluid level sensor;
determining a suction pressure in said aspiration chamber with a pressure transducer;
calculating a suction flow rate with said computer in response to said actual level of fluid, said pump speed and said suction pressure;
maintaining a desired suction flow rate in said aspiration chamber with said computer by providing a first signal to a proportional valve fluidly coupled to a pressurized gas source and a second signal to a second proportional valve fluidly coupled to a venturi vacuum generator, said first and second signals responsive to said calculated suction flow rate;
aspirating fluid from a surgical device into said aspiration chamber; and
monitoring a change in said calculated suction flow rate with said computer to detect an occlusion.

2. The method of claim 1 further comprising the step of adjusting a surgical parameter of said system with said computer in response to said monitoring step.

3. The method of claim 2 wherein said surgical parameter is selected from the group consisting of ultrasound energy, desired suction flow rate, desired suction pressure, infusion pressure, cut rate, and port open duty cycle.

4. The method of claim 1 further comprising the step of adjusting a surgical parameter of said device in response to said monitoring step.

5. A method of controlling aspiration in a microsurgical system, comprising the steps of:
providing a pump speed to a peristaltic pump with a computer;
determining an actual level of fluid in an aspiration chamber with a fluid level sensor;
determining a suction pressure in said aspiration chamber with a pressure transducer;
calculating a suction flow rate with said computer in response to said actual level of fluid, said pump speed, and said suction pressure;
maintaining a desired suction flow rate in said aspiration chamber with said computer by providing a first signal to a proportional valve fluidly coupled to a pressurized gas source and a second signal to a second proportional valve fluidly coupled to a venturi vacuum generator said first and second signals responsive to said calculated suction flow rate;
aspirating fluid from a surgical device into said aspiration chamber;
calculating a suction impedance with said computer in response to said calculated suction flow rate; and
monitoring a change in said suction impedance with said computer to detect an occlusion.

6. The method of claim 5 further comprising the step of adjusting a surgical parameter of said system with said computer in response to said monitoring step.

7. The method of claim 6 wherein said surgical parameter is selected from the group consisting of ultrasound energy, desired suction flow rate, desired suction pressure, infusion pressure, cut rate, and port open duty cycle.

8. The method of claim 5 further comprising the step of adjusting a surgical parameter of said device in response to said monitoring step.

9. The method of claim 5 further comprising the step of communicating a fluid property to a surgeon in response to said suction impedance.

* * * * *